(12) United States Patent
Maurat et al.

(10) Patent No.: US 9,072,570 B2
(45) Date of Patent: Jul. 7, 2015

(54) APPLICATION TIP

(75) Inventors: Vincent Maurat, Pessac (FR);
Marguerite Fournie,
Andernos-les-Bains (FR)

(73) Assignee: PRODUITS DENTAIRES PIERRE ROLLAND, Merignac Cedex (FR)

( * ) Notice: Subject to any disclaimer, the term of this patent is extended or adjusted under 35 U.S.C. 154(b) by 687 days.

(21) Appl. No.: 12/560,078

(22) Filed: Sep. 15, 2009

(65) Prior Publication Data

US 2011/0027753 A1 Feb. 3, 2011

(30) Foreign Application Priority Data

Jul. 30, 2009 (FR) ...................................... 09 55370

(51) Int. Cl.
*A61C 17/00* (2006.01)
*A61C 5/06* (2006.01)
*A61C 5/12* (2006.01)
*A61C 9/00* (2006.01)

(52) U.S. Cl.
CPC .................. *A61C 5/062* (2013.01); *A61C 5/122* (2013.01); *A61C 9/0026* (2013.01)

(58) Field of Classification Search
CPC .... A61C 8/0018; A61C 8/0028; A61C 5/066; A61C 5/062; A61C 5/122; A61C 9/0026; A61C 19/06; A61C 3/00; A61B 17/864; A61B 17/8822; A61B 17/8825; A61B 2017/8838; B65D 83/16; B65D 83/30; A61F 2002/30677; A61F 2002/30772; A61F 2230/0008; A61K 8/02; B01F 15/0267

USPC ........... 433/80–90, 3; 422/509, 511; 401/261, 401/266; 425/183; 604/8, 19; 427/2.1; 600/585

See application file for complete search history.

(56) References Cited

U.S. PATENT DOCUMENTS

| | | | | |
|---|---|---|---|---|
| 2,483,750 | A | * | 10/1949 | Bratrud ............................ 30/162 |
| 2,988,775 | A | * | 6/1961 | Painter et al. .................. 401/261 |
| 3,943,628 | A | * | 3/1976 | Kronman et al. ............... 433/89 |
| 5,209,731 | A | * | 5/1993 | Sterman et al. ............ 604/97.02 |
| 6,585,511 | B2 | * | 7/2003 | Dragan et al. ................... 433/90 |
| 6,616,019 | B2 | * | 9/2003 | D'Alessio et al. ............. 222/566 |
| 6,637,967 | B2 | * | 10/2003 | Bobo et al. ..................... 401/261 |
| 7,166,570 | B2 | * | 1/2007 | Hunter et al. ............... 514/21.92 |
| 7,309,310 | B2 | * | 12/2007 | Milbocker ....................... 600/30 |
| 7,325,995 | B2 | * | 2/2008 | Keller ............................ 401/266 |
| 7,855,242 | B2 | * | 12/2010 | Jia et al. ......................... 523/116 |
| 2009/0136282 | A1 | * | 5/2009 | Brown ............................... 401/1 |

\* cited by examiner

*Primary Examiner* — Cris L Rodriguez
*Assistant Examiner* — Mirayda A Aponte
(74) *Attorney, Agent, or Firm* — Workman Nydegger

(57) ABSTRACT

An application tip (100) for a viscous or pasty composition having a body (101) including a proximal end (102) that can be fastened onto a device for dispensing the composition and a distal end (103) that is provided with an outlet orifice (104), an internal duct (110) extending between the proximal and distal ends of the body. The internal duct (110) comprises at least one portion (112) of flat shape opening out at the outlet orifice (104) and includes adjacent grooves (113) in at least one of its sides.

9 Claims, 2 Drawing Sheets

APPLICATION TIP

FIELD OF THE INVENTION

The present invention relates to devices for applying viscous or pasty compositions. More particularly but not exclusively, it relates to the tips used to apply such compositions in the dental field.

BACKGROUND

During dental treatment, such as a teeth whitening operation, the patient's gums are initially protected using a viscous photo-polymerizable composition in order to form a protective barrier, also termed a gingival barrier. In order to provide a patient's gums with effective protection from the whitening compositions, the composition must be spread uniformly over the gums.

European patent document EP-A-0 956 084 describes an application tip for dental compositions that is formed by a cannula having an application end that is provided with fibrous bristles in order to facilitate spreading of the composition. However, such a tip cannot deposit a wide strip of composition that is uniform in width and thickness.

Patent documents EP-1 810 712 and US-2006/0065677 describe application tips provided with a spatula at their outlet ends to facilitate spreading of the composition. However, in the context of applying a dental composition such as a composition intended to form a gingival barrier, the spatula alone cannot ensure that the composition is deposited effectively on the gums. If the composition is not delivered to the tip outlet in sufficient quantity and with relatively uniform thickness, there is a tendency for the practician to press the spatula harder on the patient's gums in order to compensate for the lack of uniformity of the composition at the tip outlet. On pressing too hard on the spatula, there is a risk that the composition is no longer be deposited continuously onto the patient's gums, thereby leaving parts of the gums exposed. Further, since the gums are fragile, pressing too hard on them is not recommended.

SUMMARY

The aim of the present invention is to propose a novel concept for an application tip that allows viscous or pasty compositions especially for dental use to be applied in a strip with substantially uniform thickness and width.

This aim is achieved by an application tip for a viscous or pasty composition, the tip comprising a body including a proximal end that can be fastened onto a device for dispensing said composition and a distal end that is provided with an outlet orifice, an internal duct extending between the proximal and distal ends of said body, wherein the internal duct includes at least one portion of flat shape opening out at the outlet orifice, and wherein said flat portion includes adjacent grooves in at least one of its sides.

The adjacent grooves mean that a viscous or pasty composition can be distributed uniformly in the portion of the duct with a flat shape and a substantially constant quantity of composition can be delivered over the entire width of the duct portion. Thus, at the outlet orifice, a strip or ribbon of composition with a uniform width and thickness is deposited.

According to a particular characteristic of the invention, the tip further comprises a spatula placed at the distal end of the body of the tip that is beyond the outlet orifice. This spatula means that the thickness of the strip of deposited composition can be controlled. The width of the spatula is preferably greater than that of the orifice outlet. Further, it is constituted by a flexible material in order to avoid the risk of damaging sensitive surfaces such as the gums.

In a particular aspect of the invention, the tip includes an applicator portion having a profile with a rounded shape that facilitates contact and spreading over surfaces that are themselves rounded, such as the gums in particular.

In accordance with a particular aspect of the invention, the proximal end includes a LUER-LOCK® type screw thread in order to be compatible with syringes or other devices using LUER-LOCK® connections, where LUER-LOCK® types screw threads and connections are Luer lock connectors that use a male-taper fitting that mates with a female part.

The invention also provides a device for applying viscous or pasty compositions, the device comprising a syringe that can contain and deliver said composition, and being characterized in that it further comprises a tip in accordance with the invention, said tip being fastened to a free end of the syringe.

The invention also provides a method of forming a protective barrier or gingival barrier on a gum, the method comprising depositing on the gums a strip or ribbon of a viscous or pasty photo-polymerizable composition using an application tip in accordance with the invention, and photo-polymerizing said composition.

Finally, the invention further provides the use of an application tip in accordance with the invention in applying a strip or ribbon of a viscous or pasty composition.

BRIEF DESCRIPTION OF THE DRAWINGS

Other characteristics and advantages of the invention become apparent from the following description of particular modes of the invention given by way of non-limiting examples with reference to the accompanying drawings in which.

DETAILED DESCRIPTION OF VARIOUS EMBODIMENTS OF THE INVENTION

Figure 1A:
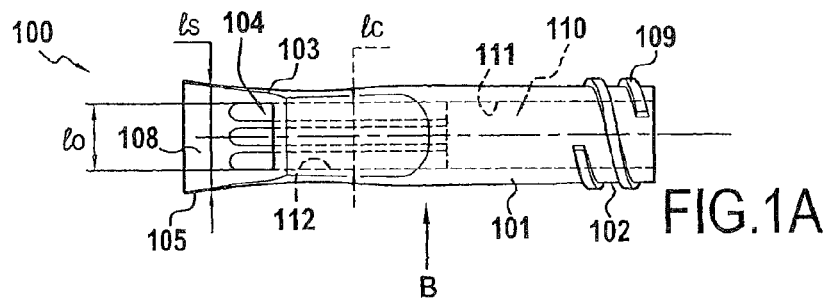
FIGS. 1A and 1B are bottom and left perspective views of an application tip in accordance with one embodiment of the invention.
Figure 1B:
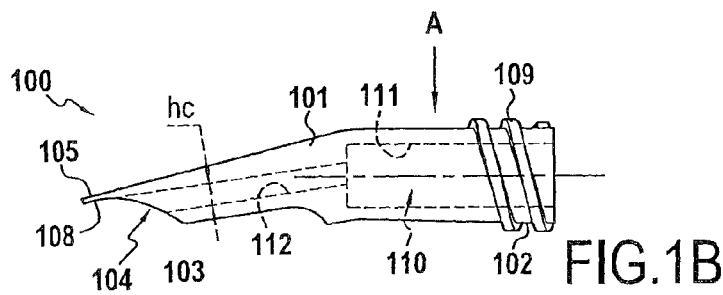
Figure 2:
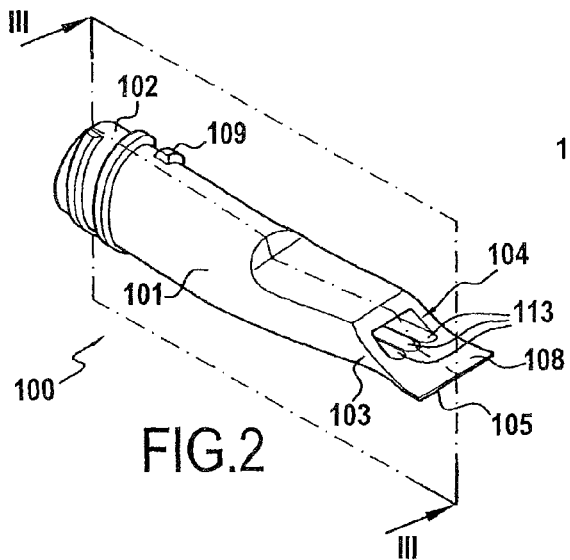
FIG. 2 is a bottom/right perspective view of an application tip in accordance with one embodiment of the invention.
Figure 3:
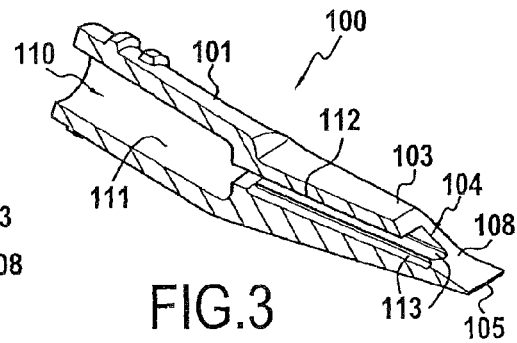
FIG. 3 is a sectional view of the tip of FIG. 2.

An advantageous application of the invention lies in depositing a composition for dental use. However, the tip of the invention may be used in other applications involving deposition of a viscous or pasty composition such as, but not exclusively, a gel or a cream.

FIGS. 1A, 1B, 2 and 3 represent an application tip 100 for depositing a viscous or pasty composition constituting one embodiment of the present invention.

The tip 100 is formed by an elongate body 101 that extends lengthwise between a proximal end 102 that can be fastened on a composition dispenser device, such as a syringe as is explained below, and a distal end 103 provided with an outlet orifice 104.

The tip 100 includes an internal duct 110 that extends between the proximal 102 and distal 103 ends. The internal duct comprises a first portion 111 that extends over a predetermined distance from the proximal end 102, and a second portion 112 that extends in line with the first portion 111 to the outlet orifice 104. In the embodiment described here, the first duct portion 111 has a circular section. However the first duct may have a section of some other shape (square, polygonal, etc).

The second duct portion 112, which is adjacent to the outlet orifice, has a width $l_c$ that is greater than its height $h_c$ in order to form a duct with a section of substantially rectangular flat shape that encourages application of the composition in the form of a strip or ribbon. For example, the duct portion has a transverse cross-section having at least one flat surface, where the at least one flat surface has a length which extends lengthwise, i.e., longitudinally along the application tip, along the second duct portion between the internal duct 110 and the outlet orifice 104. In order to ensure spreading of the composition that is controlled and uniform both as regards to width and thickness, adjacent grooves 113 are provided in the upper part of the second duct portion 112, i.e., lengthwise along the flat surface. The grooves 113 mean that the composition can be properly distributed and directed in the second duct portion 112 to the outlet orifice 104.

In a variation, adjacent grooves may be provided in the lower part of the second duct portion 112. In another variation, adjacent grooves may be provided both in the lower part and in the upper part of the second duct portion 112.

The tip 100 also includes a spatula 105 placed at the distal end 103 and extending beyond the outlet orifice 104. The spatula 105 has a width $l_c$ that is greater than the width $l_o$ of the outlet orifice 104. The spatula 105 has a flared shape such that its width $l_s$ increases gradually with distance from the outlet orifice 104 (FIG. 1A).

The spatula is flexible, meaning that since it can be readily deformed in contact with the deposition surface (FIG. 5), it can spread the deposited composition properly. The flexibility of the spatula means that the risk of damaging sensitive surfaces such as the gums during application can be avoided.

The distal end 103 and the lower part of the spatula 105 form the applicator part 108 proper of the tip, i.e. the part of the tip that is in contact with the surface onto which the composition is deposited. In the embodiment shown here, the applicator part 108 has a rounded profile (FIG. 1B) that is adapted to match and follow surfaces that themselves have a substantially rounded shape, as applies in particular with the gums.

However, the shape and geometry of the applicator part of the tip of the invention may be different in order to be adapted to the surface onto which the composition is to be applied.

In the example described here, the body 101 of the tip has a bent shape, facilitating application of the composition to rounded surfaces such as the gums. However, depending on the geometry of the surfaces onto which the composition is to be applied, the body of the tip could have different shapes.

For example, the tip of the invention may be produced by molding, using one of the following materials:
an epoxy resin of the SOMOS PROTOGEN® O-XT 18240 type;
a flexible PT8472 polyurethane type system produced by PTM&W Industries Inc;
an acrylic polymer such as that known under the trade name FULLCURE® sold by Object;
a silicone polymer such as that known under the trade name SILASTIC® distributed by Dow Corning.

The above or similar materials mean that a body can be formed for the tip that is sufficiently rigid for it to be screwed onto a syringe while allowing proper flexibility at the spatula because the material is thin at this location.

Figure 4:
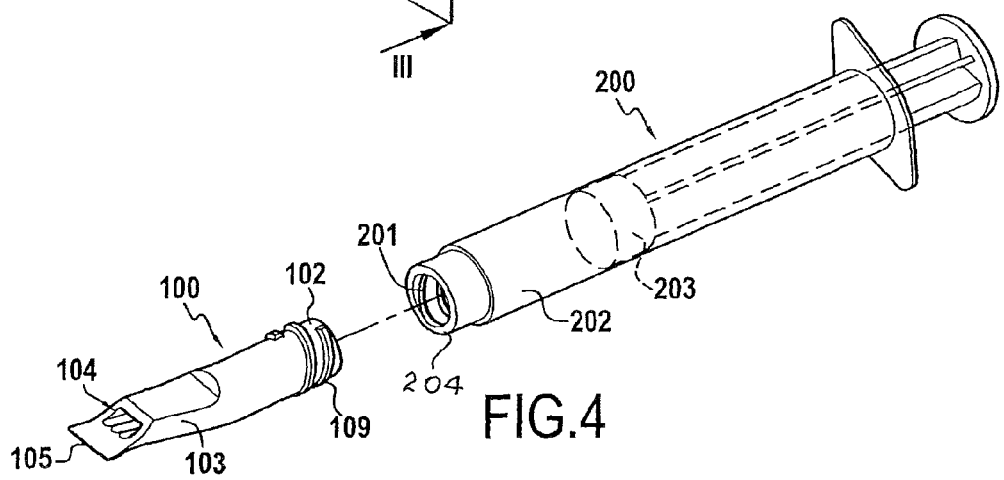
FIG. 4 is a perspective view of an application device constituted by a syringe and the tip of FIG. 2.

As can be seen in FIG. 4, the tip 100 also includes a screw thread 109 at the proximal end 102 that can cooperate with a thread 201 of a syringe 200. The proximal end 102 of the tip 100 is thus fastened to the free end 204 of the syringe 200 by screw fastening. The syringe 200 comprises a reservoir 202 for containing the viscous or pasty composition to be applied, the composition being delivered into the tip by applying pressure on a piston 203 of the syringe that advances in the reservoir 202. The first portion of the duct 111 preferably has a flow section (volumetric flow rate) that is substantially similar to that of the syringe 200 so as not to impede the composition as it leaves the syringe. Further, the second duct portion 112 preferably has a flow section that is smaller than that of the first duct portion 111 so as to optimize filling of the second duct portion with the composition arriving from the first duct portion.

The screw thread 109 is preferably a LUER-LOCK® type screw, i.e., a Luer lock, thread—this is the most widespread standard connection between a syringe and accessories, and it can cooperate with the LUER-LOCK® type thread profile 201 of the syringe 200.

Figure 5:
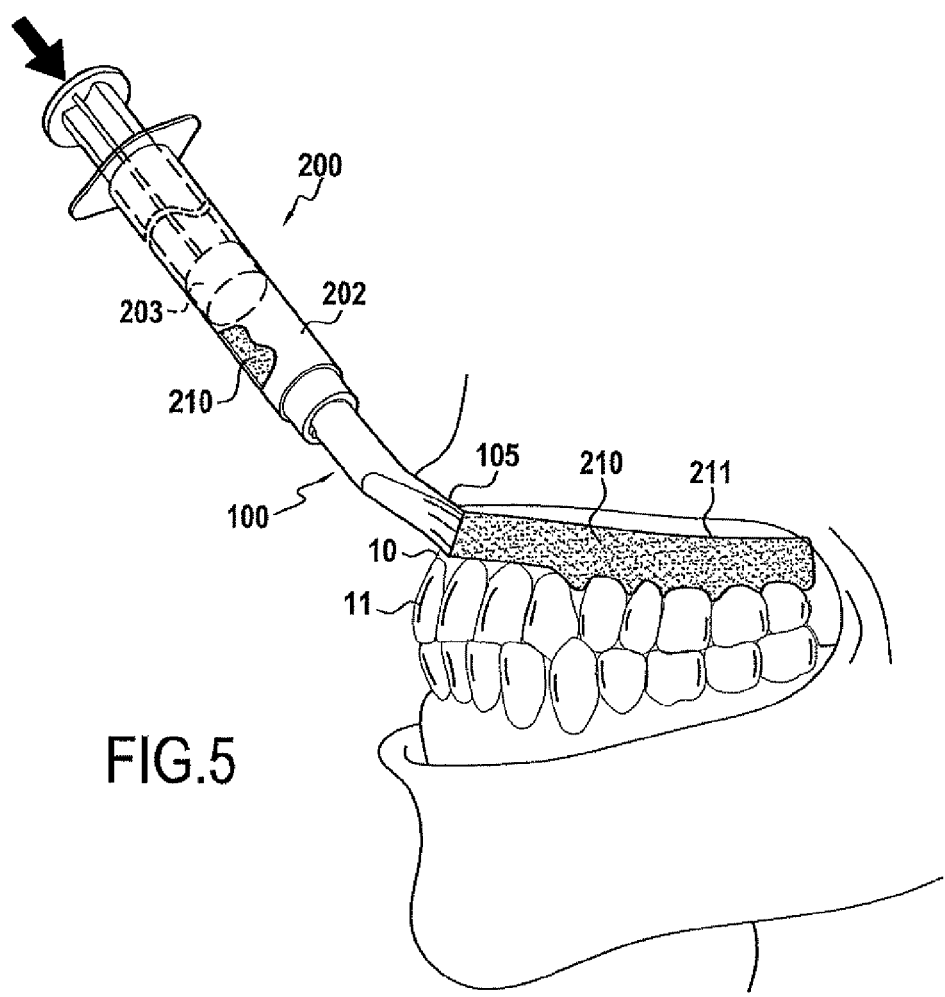
FIG. 5 is a perspective view showing a tip in accordance with the invention, being used to apply a strip or ribbon of a photo-polymerizable viscous composition in order to form a gingival barrier.
Figure 6:
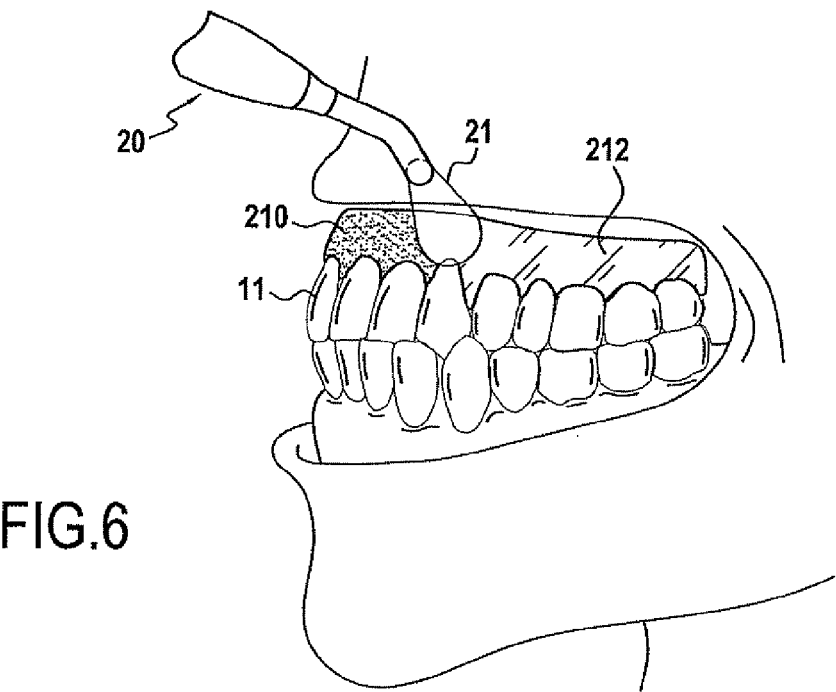
FIG. 6 is a perspective view showing the composition being photo-polymerized to form a gingival barrier.

Referring now to FIGS. 5 and 6, there is shown an example of the use of the tip of the invention in the application of a composition for dental use for forming a protective barrier or gingival barrier. In FIG. 5, the tip 100 is mounted on the syringe 200 that contains a composition 210 with a viscous or pasty texture and that is photo-polymerizable in its reservoir 202.

The composition 210 is applied to the gums 10 of a patient in the form of a strip or a ribbon 211. Because of the flat shape of the second duct portion opening out at the outlet orifice and because of the presence of the adjacent grooves, the composition 210 is delivered to the outlet of the tip in the form of a strip or ribbon 211 of uniform thickness and width.

By way of example, for application of a composition onto a surface with the dimensions of a gum, the tip of the invention may have the following dimensions:
total tip length: 33.6 mm [millimeter];
proximal end diameter (including screw thread): 7.83 mm;
width $l_c$ of second duct portion: 3.95 mm;
height $h_c$ of second duct portion: 2 mm;
maximum width $l_s$ of spatula: 7 mm.

Uniform spreading and distribution of the composition 210 over the gums 10 are also facilitated by the spatula 105.

Once the composition 210 has been applied over the whole gum 10, this is exposed to light 21 emitted by a photo-polymerization lamp 20 (FIG. 6). Under the effect of the light 21, the composition 210 polymerizes to form a protective barrier or gingival barrier 212 that is solid and that adheres to the gums 10. When photo-polymerization is complete, the gingival barrier 212 thus protects the patient's gums from other compositions used to treat the teeth 11, such as whitening compositions, for example.

The invention claimed is:

1. An application tip for a viscous or pasty composition, the application tip comprising:
an elongate body having a length and comprising a proximal end configured in a way such that the proximal end is fastenable onto a device for dispensing said composition and a distal end having a terminal outlet orifice, and an internal duct extending lengthwise of the body between the proximal end and said outlet orifice, said duct being fully opened over its cross-section and having a rectangular cross-section with a transverse width greater than a transverse height over a portion thereof extending up to and terminating at the terminal outlet orifice, said terminal outlet orifice being open and rectangular in cross-section with a transverse width greater than a transverse height that corresponds to the transverse width and height of the duct adjacent the orifice, with at least one wall of the duct extending lengthwise and widthwise in a plane from an area within the duct to the terminal outlet orifice, said at least one wall having parallel and adjacent grooves therein extending lengthwise thereof from an area within the duct to the orifice, wherein the application tip further comprises a spatula placed at the distal end of the body of the tip, said spatula extending beyond the outlet orifice, and wherein the application tip includes an applicator surface facing toward a surface onto which the composition is to be deposited, the applicator surface being formed from a portion of the distal end of the body of the tip and a surface of the spatula, the applicator surface having a rounded profile including a concave portion facing toward the surface onto which the composition is to be deposited, the concave portion extending across the terminal outlet orifice, from a portion of the spatula to a distal end of a wall of the duct opposite on the terminal outlet orifice from the spatula.

2. The application tip according to claim 1, wherein the spatula is formed from flexible material.

3. The application tip according to claim 1, including an applicator part with a profile that is rounded in shape.

4. The application tip according to claim 1, wherein the proximal end includes a Luer lock connector.

5. The application tip according to claim 1, wherein the body of the tip has a bent shape.

6. A device for applying a viscous or pasty composition, the device comprising a syringe that can contain and deliver said composition, wherein said device further includes an application tip according to claim 1, said tip being fastened to a free end of the syringe.

7. A method of forming a protective barrier or gingival barrier on a gum, the method comprising depositing a strip or ribbon of a viscous or pasty photopolymerizable composition on the gums using an application tip in accordance with claim 1 and photo-polymerizing said composition.

8. The application tip according to claim 1, wherein the width of the spatula is greater than that of the outlet orifice.

9. The application tip according to claim 1, wherein the spatula has a flared shape, and the width of the spatula increases with a distance from the outlet orifice.

* * * * *